United States Patent
McDonald

[11] 3,977,598
[45] Aug. 31, 1976

[54] CENTRIFUGE TUBE

[76] Inventor: Bernard McDonald, 7700 Seville Ave., Huntington Park, Calif. 90255

[22] Filed: Apr. 17, 1975

[21] Appl. No.: 569,059

Related U.S. Application Data

[60] Division of Ser. No. 363,383, May 24, 1973, Pat. No. 3,894,845, and a continuation-in-part of Ser. No. 375,012, June 29, 1973, Pat. No. 3,937,213.

[52] U.S. Cl. .................................. 233/26; 23/292; 215/1 R
[51] Int. Cl.² ........................................... B04B 9/12
[58] Field of Search ............... 233/1 R, 1 A, 26, 27; 23/292, 253; 128/214 D, 2 F; 215/1 R

[56] References Cited
UNITED STATES PATENTS

| | | | |
|---|---|---|---|
| 1,877,151 | 9/1932 | Turner | 23/292 |
| 2,539,082 | 1/1951 | Hustinx | 23/292 |
| 3,107,031 | 10/1963 | Adams | 215/1 R |
| 3,352,486 | 11/1967 | Gibbs | 233/26 |
| 3,452,924 | 7/1969 | Schlutz | 233/26 X |
| 3,513,976 | 5/1970 | James | 233/26 X |
| 3,874,851 | 4/1975 | Wilkins | 128/2 F |

*Primary Examiner*—George H. Krizmanich
*Attorney, Agent, or Firm*—Christie, Parker & Hale

[57] ABSTRACT

This centrifuge tube has the general shape of a conventional centrifuge tube or test tube. An external re-entrant groove is provided along an upper portion of the tube. An internal tube has an open end in the closed bottom of the centrifuge tube and is in fluid communication with a flexible external tube removably fittable into the re-entrant groove. This permits a sample to be centrifuged with the external tube in place in the groove and then the external tube can be bent down to withdraw heavy sediment from the bottom of the centrifuge tube.

1 Claim, 3 Drawing Figures

CENTRIFUGE TUBE

CROSS-REFERENCE TO RELATED APPLICATIONS

This application is a division of my U.S. patent application, Ser. No. 363,383, filed May 24, 1973 now U.S. Pat. No. 3,894,845. In addition, it is a continuation-in-part of my copending patent application, Ser. No. 375,012, filed June 29, 1973 now U.S. Pat. No. 3,937,213.

BACKGROUND

Many samples of body fluids and the like are separated in a centrifuge to isolate cells or other sediment from the supernatant liquid. It is often desirable to withdraw this heavy sediment for microscopic or other examination. Ordinarily a pipette is used to reach through the supernatant liquid and withdraw a specimen of the sediment in the bottom. Insertion of a pipette can cause mixing of the supernatant liquid and sediment, particularly if there is only a minor density difference. Decantation of the supernatant is nearly impossible and it is desirable to provide a technique for withdrawing sediment from the bottom of a centrifuge tube without disturbing the supernatant.

BRIEF SUMMARY OF THE INVENTION

There is, therefore, provided in practice of this invention according to a presently preferred embodiment a centrifuge tube open at its upper end and closed at its bottom end. An external groove extends along a portion of the length of the centrifuge tube. An internal tube has an open end in the closed bottom of the centrifuge tube and is in fluid communication with a flexible external tube that fits into the re-entrant groove on the outside of the centrifuge tube.

DRAWINGS

These and other features and advantages of the present invention will be appreciated as the same becomes better understood by reference to the following detailed description when considered in connection with the accompanying drawings wherein.

DESCRIPTION

As illustrated in the presently preferred embodiment there is a sedimentation or centrifuge tube 29 in the form of a rigid tube of conventional size and external shape for fitting in a conventional centrifuge. The centrifuge tube is open at the top and closed at the bottom much like a test tube. One side of the centrifuge tube 29 has a re-entrant groove 42 extending most of the way down the outside of the tube. An internal tube 43 dips into the very bottom portion of the centrifuge tube 29 and communicates with a flexible tube 44 on the outside of the centrifuge tube.

The tube 43 inside the centrifuge tube may be integral with the flexible tube 44 on the outside. This is particularly appropriate when the centrifuge tube is molded plastic since a flexible plastic tube can be molded through the side of the centrifuge tube to dip into the bottom thereof and also fit into the re-entrant groove. If a glass centrifuge tube is used a flexible plastic tube may be cemented through the wall thereof to fit into the re-entrant groove and dip into the bottom of the centrifuge tube. If desired the inside tube may be rigid and the outside tube flexible with a joint therebetween at a convenient location, preferably outside the centrifuge tube.

During fluid collection and centrifuging the flexible tube 44 reposes in the elongated re-entrant groove 42 in the side of the sedimentation tube with a reasonably snug fit. Upon centrifuging heavy portions and sediment in the fluid collect in the bottom of the centrifuge tube and it is these portions that are of interest for microscopic examination. The balance of the liquid in the upper portions of the sedimentation tube is typically of no additional interest.

Figure 3:
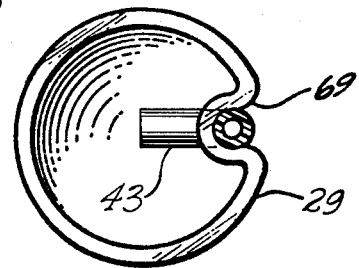
FIG. 3 is a top view of the centrifuge tube.
Figure 1:
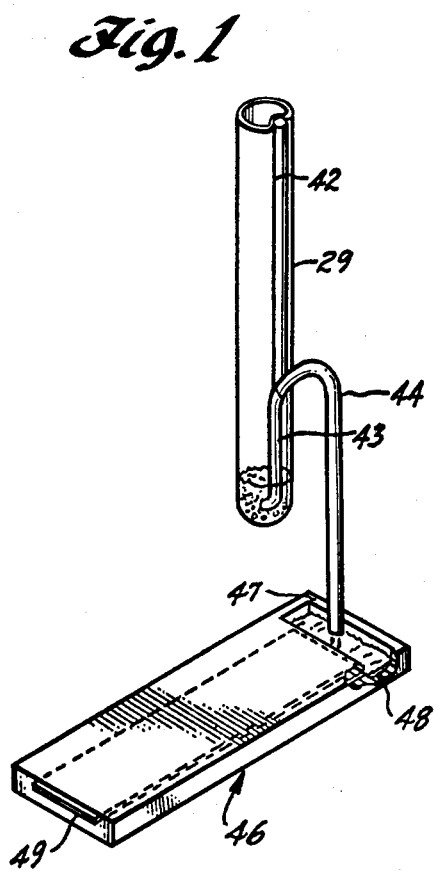
FIG. 1 illustrates a centrifuge tube constructed according to principles of this invention and a microscope slide useful with it.
Figure 2:
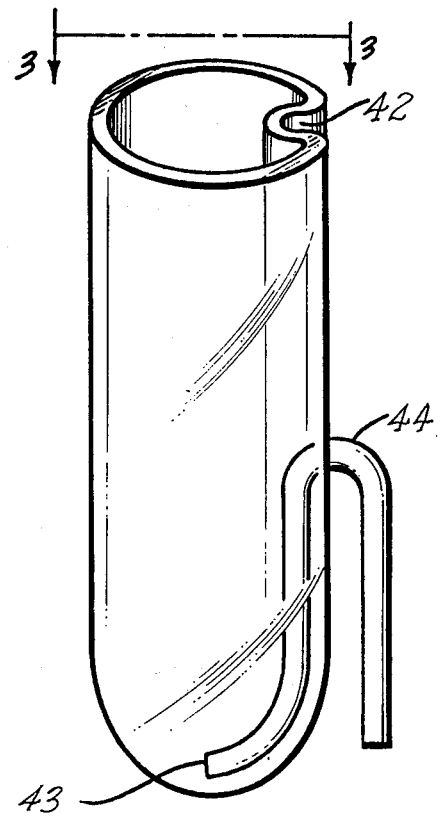
FIG. 2 is an enlarged view of the centrifuge tube.

After centrifuging, the sediment in the bottom is transferred to a microscope slide such as the special self-smearing slide 46 illustrated in FIG. 1. The flexible tube 44 is removed from the groove 42 and bent down so that a small amount of the liquid in the centrifuge tube including the heavy portions in the bottom are siphoned out to be examined microscopically. By siphoning from the bottom, mixing of sediment in the bottom with supernatant liquid is avoided.

Typically in the past the fluid to be examined has been spread manually across a rectangle of glass or transparent plastic using another microscope slide as a spreader. A dye may be applied for staining portions of the fluid to be examined and an adhesive such as balsam oil is added. This is then covered by a cover slip before microscopic examination. In the special slide 46 illustrated in FIG. 1, dyeing and uniform spreading is automatically achieved. A fluid, such as sediment and liquid from the bottom of the centrifuge tube 29, is placed in a compartment 47 at one end of the transparent slide 46. A porous material such as blotting paper containing a soluble dye resides in the bottom portion of the compartment 47. The fluid extracts a portion of the dye from the porous material 48 upon contact therewith. Preservatives or other reagents that may react with the fluid may be contained in the porous body. The fluid then flows into a narrow slit or capillary passage 49 extending along the slide by normal capillary action and no additional handling is required before microscopic examination.

It will be noted that the layer of the fluid is thus made uniformly thin and is self-staining, both of which contribute to minimal handling and risk of contamination of the fluid being examined.

If during the course of taking or handling a sample it is desirable that the centrifuge tube 29 be evacuated, a suitably conformed stopper may be provided in the tube or the re-entrant groove 42 may terminate below the upper portion of the centrifuge tube so that a circular stopper is suitable. In addition the upper or free end of the flexible tube 44 should be sealed.

Although limited embodiments of centrifuge tube with means for withdrawing sediment from the bottom have been described and illustrated herein, many modifications and variations will be apparent to one skilled in the art. It is therefore to be understood that within the scope of the appended claims the invention may be practiced otherwise than as specifically described.

What is claimed is:

1. A centrifuge tube comprising:
   an elongated tube open at its upper end and closed at its bottom end;
   an external re-entrant groove along a portion of the tube;
   an internal tube having an open end in the bottom end of the elongated tube; and
   a flexible external tube in fluid communication with the internal tube and removably fittable in the re-entrant groove.

* * * * *